United States Patent
Ishikawa et al.

(10) Patent No.: US 8,012,218 B2
(45) Date of Patent: Sep. 6, 2011

(54) MEDICAL BONE PROSTHETIC MATERIAL AND PROCESS FOR PRODUCING THE SAME

(75) Inventors: Kunio Ishikawa, Shime-machi (JP); Shigeki Matsuya, Fukuoka (JP); Masaharu Nakagawa, Fukuoka (JP); Kouichi Udou, Fukouka (JP)

(73) Assignee: Kyushu University, National University Corporation, Fukuoka (JP)

( * ) Notice: Subject to any disclaimer, the term of this patent is extended or adjusted under 35 U.S.C. 154(b) by 776 days.

(21) Appl. No.: 10/562,711

(22) PCT Filed: Jun. 22, 2004

(86) PCT No.: PCT/JP2004/008738
§ 371 (c)(1),
(2), (4) Date: Apr. 18, 2006

(87) PCT Pub. No.: WO2004/112856
PCT Pub. Date: Dec. 29, 2004

(65) Prior Publication Data
US 2006/0225619 A1    Oct. 12, 2006

(30) Foreign Application Priority Data
Jun. 24, 2003   (JP) ................................. 2003-179257

(51) Int. Cl.
*A61F 2/28*   (2006.01)
(52) U.S. Cl. ..................................... 623/23.61; 423/308
(58) Field of Classification Search ............... 623/23.61, 623/23.6–23.63; 423/267, 308–311
See application file for complete search history.

(56) References Cited

U.S. PATENT DOCUMENTS

| | | | | |
|---|---|---|---|---|
| 3,764,656 A | * | 10/1973 | Carlson | 423/311 |
| 4,472,365 A | * | 9/1984 | Michel | 423/267 |
| 4,612,053 A | * | 9/1986 | Brown et al. | 106/35 |
| 4,828,823 A | * | 5/1989 | Li | 424/52 |
| 5,017,518 A | * | 5/1991 | Hirayama et al. | 501/1 |
| 5,071,434 A | | 12/1991 | Tsuzuki et al. | |
| 5,952,010 A | * | 9/1999 | Constantz | 424/602 |

(Continued)

FOREIGN PATENT DOCUMENTS

JP     07-061861     3/1995

(Continued)

OTHER PUBLICATIONS

Hall, Brian. "Experimental investigation on Pore size and Pore Distribution," Bone: Fracture Repair and Regeneration. 1999. CRC Press, Inc. vol. 5, pp. 161-162. Accessed through Google books on Jul. 15, 2009.*

(Continued)

*Primary Examiner* — Eduardo C Robert
*Assistant Examiner* — Steven J Cotroneo
(74) *Attorney, Agent, or Firm* — Fay Sharpe LLP (57) ABSTRACT

There is disclosed a bone substitute material for medical use which satisfies all the requirements of (1) no histotoxicity, (2) osteoconductivity, (3) bone replacement capability, and (4) mechanical strength necessary for a bone reconstruction operation. The bone substitute material for medical use is predominantly composed of carbonate apatite and produced through the formation of carbonate apatite by contacting a block of calcium compound with a phosphate-containing solution, wherein the calcium compound block contains substantially no powders, and at least one of said calcium compound block and said phosphate solution contains a carbonate group, without any sintering. The block of calcium compound is preferably one prepared using an artificially synthesized calcium compound, most preferably a foamed calcium compound.

14 Claims, 5 Drawing Sheets

U.S. PATENT DOCUMENTS

| | | | |
|---|---|---|---|
| 6,027,742 A * | 2/2000 | Lee et al. | 423/308 |
| 6,210,715 B1 * | 4/2001 | Starling et al. | 423/308 |
| 7,150,862 B2 * | 12/2006 | Ishikawa et al. | 423/308 |
| 2003/0055512 A1 * | 3/2003 | Genin et al. | 623/23.56 |
| 2004/0198909 A1 * | 10/2004 | Breitscheidel et al. | 525/165 |
| 2006/0147547 A1 * | 7/2006 | Yayon | 424/602 |

FOREIGN PATENT DOCUMENTS

| | | | |
|---|---|---|---|
| JP | 10-036106 A | | 2/1998 |
| JP | 11-180705 A | | 7/1999 |
| JP | 11180705 | * | 7/1999 |

OTHER PUBLICATIONS

"Block" Merriam Webster Online dictionary. 2009. Merriam-Webster Online. Jul. 15, 2009 <http://www.merriam-webster.com/dictionary/block>.*

Hattori, et al., *Development of Porous Ceramics*, CMC Co. Ltd., pp. 227-294, Sections 9.3 (9.3-9.3.4) (1991).

* cited by examiner

MEDICAL BONE PROSTHETIC MATERIAL AND PROCESS FOR PRODUCING THE SAME

TECHNICAL FIELD

The present invention relates to a bone substitute material for medical use and a method of producing the same, and more particularly, to a bone substitute material for use in the regeneration or repair of the hard tissue.

BACKGROUND ART

In medical and dental fields, there are many cases where a bone defect caused by a disease or injury must be repaired or regenerated. The first possible approach to repair the bone defect may be an autograft bone transplantation, but this approach causes problems including an invasion into the sound tissue owing to the autograft bone as well as quantitative and morphological limitation of the collected bone. Artificially produced bone substitute materials are therefore clinically employed.

It is desired for a bone substitute material to combine the features of (1) no histotoxicity, (2) osteoconductivity, (3) bone replacement capability, and (4) mechanical strength required in a bone reconstruction operation. No histotoxicity is indispensable to a biomaterial. Histotoxicity is evaluated from macroscopical or histopathological indication of inflammation in an experimental animal implanted with a bone substitute material. Histotoxicity is also influenced by the mechanical strength of a bone substitute material. There occurs crystalline inflammation if the mechanical strength of the bone substitute material is low so that the material is partly disintegrated during the bone reconstruction into powdery form and remains within the bone defect. Osteoconductivity is defined as the property of a bone substitute material applied to a bone defect to promote the formation of new bone tissue from the site of application to the bone so as to cover the bone substitute material. Osteoconductivity is a crucial property of a bone substitute material, the presence or absence of which is evaluated on histopathological examination of an experimental animal implanted with the bone substitute material. It is generally considered that if the differentiation of osteoblast cells cultured on a bone substitute material is promoted, then the material possesses osteoconductivity.

Bone replacement capability is crucial to a bone substitute material. In the bone replacement by the bone substitute material, it is ideal that the resorbing process by osteoclast cells and the bone formation process by osteoblast cells proceed as in the remodeling. Replacement of bone by the bone substitute material is histopathologically evaluated with an experimental animal implanted with the bone substitute material. However, the evaluation of the bone replacement capability with such experimental animals requires much time for the experiments. An osteoconductive material operates on the principle of replacing bone as resorption by osteoclast cells proceds. The possible bone replacement capability of such a material can therefore be ascertained by checking resorption cavities formed by the osteoclast cells on the material. It is also crucial for a bone substitute material to have the mechanical strength necessary for a bone repair operation. While the degree of the required mechanical strength is not necessarily definite, it is of course indispensable for the material to possess a mechanical strength resistant to the implantation.

Hydroxyapatite is currently the most-studied bone substitute material. The primary inorganic component of the bone, tooth or other hard tissue of verterbrates including humans is an apatite basically composed of hydroxyapatite, $Ca_{10}(PO_4)_6(OH)_2$. Thus, there is clinically used a bone substitute material composed of sintered hydroxyapatite prepared by sintering chemically synthesized hydroxyapatite. While sintered hydroxyapatite exhibits osteoconductivity and therefore is a very useful bone substitute material, it is an unresorbable material which will not be resorbed at bone defect sites even over the passage of time. Bone exhibits biological functions such as hematopoiesis, and it is ideal to use a bone substitute material which is capable of replacing bone.

Under the circumstances are also clinically used as bone substitute material such materials as β-tricalcium phosphate, calcium sulfate, calcium carbonate and the like. These materials exhibit resorbability but are not osteoconductive, or are less osteoconductive than hydroxyapatite. In addition, when there is used a resorbing material such as β-tricalcium phosphate, calcium sulfate or calcium carbonate, the resorption is caused by physicochemical dissolution or extraneous giant cells and the mechanism of the resorption is not linked with bone formation by osteoblast cells. Thus, in a case where bone defect is severe or the bone defect site is inferior in bone formation ability because of aging and other reasons, the bone resorption proceeds even before the bone formation is sufficiently carried out, resulting in the bone substitute material being consumed prior to its replacement of bone, and the bone defect comes to be repaired by fibrous connective tissue.

In the case of an autogenous bone transplantation, the mechanism of bone replacement by the transplanted bone is the same as that of the remodeling of living bone. Thus, bone resorption is advanced by osteoclast cells while bone formation is accomplished by osteoblast cells. In sintered hydroxyapatite which exhibits osteoconductivity, although the process of bone formation by osteoblast cells proceeds, no bone replacement occurs because bone is not resorbed by osteoclast cells. Resorption by osteoclasts is accomplished through the formation of Howship's lacunae, in the interior of which there is induced a low pH resulting in the decomposition of bone apatite. Bone apatite is carbonate apatite containing a carbonate group and therefore decomposable in the low pH environment induced by osteoclast cells. By contrast, since sintered hydroxyapatite contains no carbonate group, it is not decomposed in the low pH environment induced by osteoclast cells. Thus, sintered hydroxyapatie, which is currently put into clinical use as a bone substitute material, has no bone replacement capability partly because it is not a carbonate-containing apatite.

In view of there considerations, carbonate apatite would be an ideal bone substitute material. However, no technology for producing carbonate apatite practically utilizable as a bone substitute material has not been established. More specifically, known or proposed uses of carbonate apatite are limited to those as adsorbents or carriers for biomaterials and the like, and as restorative materials for bones and teeth [for example, Japanese Patent Application Publication No. 1995-61861 (Patent Reference No. 1), Japanese Patent Application Publication No. 1998-36106 (Patent Reference No. 2), Japanese Patent Application Publication No. 1999-180705 (Patent Reference No. 3)]. The latter use is only for the purpose of filling the defect sites of bones or teeth, and no material primarily composed of carbonate apatite has been developed which satisfies the prerequisites of a bone substitute material for medical use, including bone replacement capability and no histotoxicity without causing inflammation.

Patent Reference No. 1: Japanese Patent Application Publication No. 1995-61861

Patent Reference No. 2: Japanese Patent Application Publication No. 1998-36106

Patent Reference No. 3: Japanese Patent Application No. 1999-180705

DISCLOSURE OF THE INVENTION

Subjects to be Solved by the Invention

The object of the present invention is to provide a bone substitute material for medical use which satisfies all the requirements of (1) no histotoxicity, (2) osteoconductivity, (3) bone replacement capability, and (4) mechanical strength necessary for a bone reconstruction operation.

Through extensive studies, the present inventors discovered that there can be obtained a bone substitute material for medical use satisfying all the above-mentioned requirements by forming carbonate apatite from a calcium compound and a phosphate solution (an aqueous solution) in the presence of carbonate functional group under a specific condition, thereby achieving the present invention.

Thus, according to the present invention there is provided a method of producing a bone substitute material predominantly composed of carbonate apatite for medical use, which comprises the step of forming carbonate apatite by contacting a block of calcium compound with a phosphate-containing solution, wherein said calcium compound block contains substantially no powders, wherein at least one of said calcium compound block and said phosphate solution contains a carbonate group, and wherein the method does not include any sintering step.

In a preferred embodiment of the present invention, the block of calcium compound is one prepared using an artificially synthesized calcium compound, most preferably a foamed calcium compound.

The present invention also provides a bone substitute material predominantly composed of carbonate apatite for medical use, produced by the above-mentioned method, which contains carbonate group in an amount of 0.5% or more by weight.

Advantageous Effects of the Invention

The present invention provides a bone substitute material for medical use which satisfies all the requirements of (1) no histotoxicity, (2) osteoconductivity, (3) bone replacement capability, and (4) mechanical strength necessary for a bone reconstruction operation.

BEST MODE FOR CARRYING OUT THE INVENTION

The present invention is directed to the formation of carbonate apatite by contacting a calcium compound and a phosphate solution in the presence of carbonate group, which is characterized by the below-mentioned matters (I) to (III), thereby realizing for the first time a bone substitute material for medical use satisfying all the requirements of (1) no histotoxicity, (2) osteoconductivity, (3) bone replacement capability, and (4) mechanical strength necessary for a bone prosthesis operation.

(I) The first characteristic feature of the method of producing a bone substitute material for medical use according to the present invention resides in the utilization of a block of calcium compound containing substantially no powders, as the starting calcium compound. As used herein, the term "block" refers to a substance which is in solid state but is not powdery, as exemplified by granule, solid and porous bodies. Thus, the block has a number-averaged particle diameter (particle size) of preferably 0.2 mm or larger, most preferably 0.5 mm or larger, and the most preferably and completely satisfactorily 1 mm or larger. A particularly preferred example of calcium compound for use in the present invention is a foamed calcium compound. As used herein with respect to the present invention, by the phrase "containing substantially no powders" is meant that the block as mentioned above contains powders with a diameter of 20 μm or smaller in an amount of less than 1% by weight.

A surprising discovery of the present inventors is that the utilization of such "a block of calcium compound containing substantially no powders" can produce a bone substitute material having no histotoxicity without causing inflammatory reaction. This is possibly because, on implanting the bone substitute material, phagocytes such as exogenous giant cells englobe carbonate apatite powder particles of a small size, thereby not inducing the inflammatory response. In terms of histocompatibility, the powders with a diameter of 20 μm or smaller which may be contained in the block material is preferably less than 0.8% by weight, and more preferably less than 0.5% by weight. By contrast, in the conventional uses of carbonate apatite such as in adsorbents, the starting calcium compound is in powdery state. For example, in Japanese Patent Application Publication No. 1998-36106 (Patent Reference No. 2) it is required that calcium carbonate as the raw material should have an average particle diameter in the range of 1 to 50 μm. Calcium carbonate from such powdery starting material will never produce a practical bone substitute material to which the present invention is directed.

(II) The second characteristic feature of the method of producing a bone prosthesis for medical use according to the present invention is that it only comprises the step of forming carbonate apatite by contacting a calcium compound, as explained in the above (I), with a phosphate solution, under the condition where at least one of the calcium compound and the phosphate solution contains carbonate group, without any subsequent step of sintering.

In a reaction system to which the present invention is directed, wherein carbonate apatite is thermodynamically stable as compared with carbonate calcium, there is formed carbonate apatite with a sufficient hardness, even at a low temperature at which sintering will not take place. Conversely, sintering will not produce the desired carbonate apatite because carbonate group is irreversibly removed during the sintering step. In addition, sintering will advance the crystallinity which decreases the specific surface area, resulting in difficulty in resorption by osteoclast cells as well as no or extremely slow bone replacement. Thus, sintered apatite carbonate as conventionally proposed (for example, the one as described in Japanese Patent Application Publication No. 1995-61861, Patent Reference No. 1, in which powdery apatite carbonate is sintered at a temperature of 600 to 850° C.) is not effective for use in a bone substitute material for medical use of the present invention having an excellent bone replacement capability.

(III) In order to obtain a bone substitute material for medical use according to the invention which satisfies all the above-mentioned requirements, it is necessary to take into consideration the purity of a calcium compound as the starting material, in addition to the aforesaid matters (I) and (II).

The leading source of histotoxicity causing inflammation in a bone prosthesis is impurities or antigenic substances contained in the starting calcium compound. In this respect, as the starting calcium material for use in the present invention is preferred an artificially synthesized calcium compound since it is intrinsically low in impurities. By contrast, it has been hitherto proposed that carbonate apatite be produced through the fragmentation of naturally occurring calcium compounds. For example, in Japanese Patent Application Publication No. 1999-180705 (Patent Reference No. 3), there are used pulverized limestones or the like as the starting material of apatite carbonate apatite for use in adsorbents or carriers of biomaterials. However, such naturally occurring materials cannot produce a bone substitute material of the present invention which does not cause inflammation due to histotoxicity, because they contain inherently natural impurities in addition to the unfavorable powders (those having a diameter of 20 μm or smaller) as explained in the above (I).

Embodiments of the present invention will be detailed below with reference to the constitutional elements of the bone substitute material and the method of producing the same according to the present invention.

As used herein with respect to the present invention, "an artificially synthesized calcium compound" refers to a calcium compound which has been synthesized by a chemical method or the like, such as a reagent. A naturally occurring or organism-derived calcium compound is not "the artificially synthesized" material. For example, while natural gypsum powders or bone meals are calcium compounds, they are not artificially synthesized calcium compounds. However, a calcium compound which has been produced by processing natural gypsum, bone or the like via, for example, a dissolution-refining process is an artificially synthesized compound.

As used herein with respect to the present invention, "a calcium compound" refers to a calcium-containing compound, exemplified by metal calcium, calcium hydroxide, calcium carbonate, calcium chloride, calcium acetate, calcium benzoate, calcium fluoride, calcium formate, calcium gluconate, calcium hydride, calcium iodide, calcium calcium lactate, apatite, tricalcium phosphate, tetracalcium phosphate, calcium hydrogenphosphate, calcium silicate, and the like. A single calcium compound can be used, while a mixture of a plurality of calcium compounds can also be used.

As used herein with respect to the present invention, "a phosphate" refers to a phosphate group-containing compound, exemplified by phosphoric acid, triammonium phosphate, tripotassium phosphate, trisodium phosphate, disodium ammoniumphosphate, sodium diammoniumphosphate, ammonium dihydrogenphosphate, potassium dihydrogenphosphate, sodium dihydrogenphosphate, trimagnesiumphosphate, ammonium sodium hydrogenphosphate, diammonium hydrogenphosphate, dipotassium hydrogenphosphate, disodium hydrogenphosphate, magnesium hydrogenphosphate-tridiacetyl phosphate, diphenyl phosphate, dimethyl phosphate, cellulose phosphate, ferrous phosphate, ferric phosphate, tetrabutylammonium phosphate, copper phosphate, triethyl phosphate, tricresyl phosphate, tris-trimethylsilyl phosphate, triphenyl phosphate, tributyl phosphate, trimethyl phosphate, guanidine phosphate, cobalt phosphate, and the like. A single phosphate-containing compound can be used, while a mixture of a plurality of phosphate-containing compounds can also be used.

In the present invention, use of a carbonate group-containing compound ensures that at least one of the calcium compound block and the phosphate solution contains carbonate group(s). As used herein, "a carbonate group-containing compound" refers to carbon dioxide ($CO_2$) or a compound of carbonate group ($CO_3^{2-}$) and cation, exemplified by carbon dioxide gas, dry ice, sodium hydrogencarbonate, disodium carbonate, potassium hydrogencarbonate, dipotassium carbonate, ammonium hydrogencarbonate, diammonium carbonate, calcium carbonate, and the like. A single carbonate group-containing can be used, while a mixture of a plurality of carbonate group-containing compounds can also be used.

As used herein with respect to the present invention, "apatite" refers to a compound having a basic structure expressed by the formula $A_{10}(BO_4)_6C_2$, wherein A denotes $Ca^{2+}$, $Cd^{2+}$, $Sr^{2+}$, $Ba^{2+}$, $Pb^{2+}$, $ZN^{2+}$, $Mg^{2+}$, $Mn^{2+}$, $Fe^{2+}$, $H^+$, $H_3O^+$, $Na^+$, $K^+$, $Al^{3+}$, $Y^{3+}$, $Ce^{3+}$, $Nd^{3+}$, $La^{3+}$, $C^{4+}$ or the like, $BO_4$ denotes $PO_4^{3-}$, $CO_3^{2-}$, $CrO_4^{3-}$, $AsO_4^{3-}$, $VO_4^{3-}$, $UO_4^{3-}$, $SO_4^{2-}$, $SiO_4^{4-}$, $GeO_4^{4-}$ or the like, C denotes $OH^-$, $OD^-$, $F^-$, $Br^-$, $BO^{2-}$, $CO_3^{2-}$, $O^{2-}$, or the like. As used herein with respect to the present invention, "hydroxyapatite" is $Ca_{10}(PO_4)_6(OH)_2$. As used herein with respect to the present invention, "carbonate apatite (apatite carbonate)" refers to an apatite in which a part or all of phosphate groups or hydroxyl groups therein are replaced with carbonate groups. The apatite in which phosphate groups are replaced with carbonate groups are called B-type carbonate apatite, while the apatite in which hydroxyl groups are replaced with carbonate groups are called A-type carbonate apatite.

As used herein with respect to the present invention, "foamed or foamed-shaped" refers to a three dimensional structure with continuous pores (the so-called sponge) such as in polyurethane foam.

A calcium compound block for use in the present invention can be produced, for example, by the calcinations of an artificially synthesized calcium compound, the hardening reaction of an air-hardening cement or the hardening reaction of a hydraulic cement.

The production of a calcium compound block by the calcination of a calcium compound may be carried out, for example, as follows: Tricalcium phosphate powders are compression-molded uniaxially, followed by calcining the resultant at 1500° C. for six hours, so as to produce tricalcium phosphate block. In the present invention, the production of such calcium phosphate block is for the purpose of providing a calcium component for a bone substitute material for medical use which is predominantly composed carbonate apatite, and therefore there is no need of a special device such as HIP or CIP for the prevention of the elimination of carbonate group, although the use of such device is not exactly excluded. Thus, since there is no need for HIP or CIP, the cost of production is low, making mass production possible, while there can be produced a bone substitute material in a desired shape.

The production of a calcium compound block by the hardening reaction of an air-hardening cement is exemplified by the reaction of calcium hydroxide and carbon dioxide: Calcium hydroxide is compression-molded uniaxially, and then the resultant compressed body is rendered to react with carbon dioxide under a stream of steam, thereby producing calcium carbonate block as precipitate, in which the compressed calcium hydroxide is partly or wholly replaced by calcium carbonate.

The production of a calcium compound block by the hardening reaction of a hydraulic cement is exemplified by the use of gypsum: Gypsum is kneaded with water, and the resultant is poured into a desired mold where the gypsum hardens to produce calcium sulfate block. The production of such calcium compound block from a hydraulic cement such as gypsum is advantageous in that it enables the production of a calcium compound block in a desired shape in an easy manner.

Calcium compound block occurs even naturally in abundance, for example, as coral, marble, natural gypsum or the like. However as mentioned previously, these naturally occurring calcium compounds are not suitable as a biomaterial because of impurities contained, and therefore in the production of the calcium compound for use in the present invention there must be used a highly pure starting material which has been artificially synthesized through a chemical synthesis or the like. Likewise, organism-derived materials are not suitable as the biomaterial because of antigenicity.

While there is no specific restriction on the shape of the calcium compound block, a porous shape is preferred since it is advantageous in accelerating bone replacement rate. In the case of a porous body, the porosity is preferably 10% or over, more preferably 30% or over, and the most preferably 50% or over. Particularly preferred calcium compound block is a foamed-shaped one because it provides a bone substitute material with an accelerated bone replacement. A foamed calcium compound block can be produced by a known method, for example, by the method as described in "Development of Porous Ceramics" (Edited by S. Hattori and A. Yamanaka, Published by CMC Co. Ltd., Pages 277-294 (1991)). More specifically, cell membrane-removed soft polyurethane foam is immersed in a calcium compound suspension, thereby rendering the calcium compound adhered on the surface of the trabecula of the polyurethane foam. Dried calcium compound-adhered polyurethane foam is calcined at a desired temperature to sinter the calcium compound while burning out the polyurethane foam, thereby producing the foamed calcium compound.

A continuous pore foamed structure is quite useful in the method of producing a bone substitute material according to the present invention, in which a foamed calcium compound block is used so that bone cells penetrate into the interior of the block effecting three-dimensional bone replacement. In view of the penetration of bone cells, the foamed calcium compound block has an average pore diameter preferably in the range of 50 μm to 100 μm, more preferably in the range of 100 m to 500 μm, and the most preferably in the range of 200 μm to 300 μm.

The calcium compound block produced in the above-mentioned manner is then brought into to contact with a solution containing a phosphate. The phosphate solution generally has a pH of 4.5 or higher. The contact is carried out, for example, by immersing the calcium compound in the solution or by spraying the solution upon the calcium compound. In general the immersion is the most convenient and economical In contacting a calcium compound block with a phosphate-containing solution, in the case where the calcium compound block is of a composition not containing carbonate group, it is indispensable to add a carbonate group-containing component to the phosphate-containing solution. In the case of a carbonate group-containing calcium compound block such as calcium carbonate block, it is not necessarily required for the phosphate-containing solution to contain carbonate group. However, it is quite acceptable for the phosphate-containing solution also to contain carbonate group for the purpose of adjusting the carbonate group content of the bone substitute material to be produced. A carbonate group-containing component may be dissolved in the phosphate-containing solution or may be added thereto even in an amount exceeding saturation. In any case, it is required that the carbonate group content be sufficient for the bone substitute material to be produced.

While there is no restriction on the temperature at which a calcium compound block is contacted with a phosphate-containing solution, the higher is the temperature, the more rapidly proceeds the production of the bone substitute material for medical use predominantly composed of carbonate apatite. Thus, the reaction temperature is preferably 50° C. or higher, and more preferably 80° C. or higher. Hydrothermal synthesis at 100° C. or higher is particularly preferred because the carbonate apatite formation proceeds even internally and the production rate is accelerated as well. However, as described previously, no sintering step is required in the method of the production of a bone substitute material according to the present invention.

There are no restrictions on the period of time for which the calcium compound block is contacted with the phosphate-containing solution, either. Such period of time for the contact can be determined as deemed appropriate depending upon the composition of the bone substitute material for medical use to be produced.

The mechanism has not yet been completely elucidated by which a bone substitute material for medical use, predominantly composed of carbonate apatite, can be produced in accordance with the method of the present invention. It is however considered, as discussed previously, that in a case where carbonate group is present, carbonate apatite assumes thermodynamically the most stable phase, and therefore the calcium compound is converted to carbonate apatite.

While no particular restrictions are imposed on the carbonate apatite content in the bone substitute material produced, it is preferred, in view of the bone replacement rate and other factors, that carbonate apatite content in the composition be 50% or more by weight, and more preferably 70% by weight in the composition. It is particularly preferred that carbonate apatite is contained in 90% or more by weight in the composition.

The carbonate group content in the bone substitute material produced exerts a large influence on the bone replacement rate. As the carbonate group content increases, the bone replacement rate accelerates. The present invention enables the production of carbonate apatite having a carbonate group content of 0.5% or more by weight with a highly increased bone replacement rate as compared with the conventionally known sintered hydroxyapatite. The carbonate group content in the bone substitute material is preferably 2% or more by weight, more preferably 4% or more by weight and the most preferably 6% or more by weight.

While the present invention will be explained in more detail with reference to Examples and Comparative Examples given below, the present invention is not limited to such Examples.

With respect to powders having a particle diameter of 20 μm or smaller contained in the carbonate apatite blocks prepared in the Examples and the Comparative Examples, the percentage of powder content was determined as follows: Carbonate apatite blocks weighing about 10 g were immersed in 200 ml of distilled water, followed by stirring carefully with a stirring rod so that the carbonate apatite blocks did not collide with the vessel or the stirring rod. Then, the total distilled water with the carbonate apatite blocks immersed therein was sifted through a 140-mesh sieve, followed by flushing the carbonate apatite blocks standing on the 140-mesh sieve with 100 ml water. This operation was repeated three times. The distilled water and the powders sifted through the 140-mesh sieve were then filtered through six different filter papers as standardized by JIS P3801, followed by drying and weighing operations. The dried powders were suspended in distilled water to analyze pore size distribution using a sedimentation particle size analyzer. Thus, with respect to powders having a particle size (particle diameter) of 20 μm or smaller contained in carbonate apatite, the powder content was determined by the percentage of such powders in the distribution as well as the total weight of the carbonate apatite sifted through the 140-mesh sieve.

Example 1

Hemihydrated calcium sulfate (Nacalai Tesque Inc.) was kneaded with distilled water at a ratio of the water of 0.4 (ml/g) to produce calcium sulfate blocks. The thus prepared calcium sulfate was immersed in a 1M diammonium hydrogenphosphate solution (in which ammonium carbonate had been suspended) for two days at 80° C.

Figure 1:
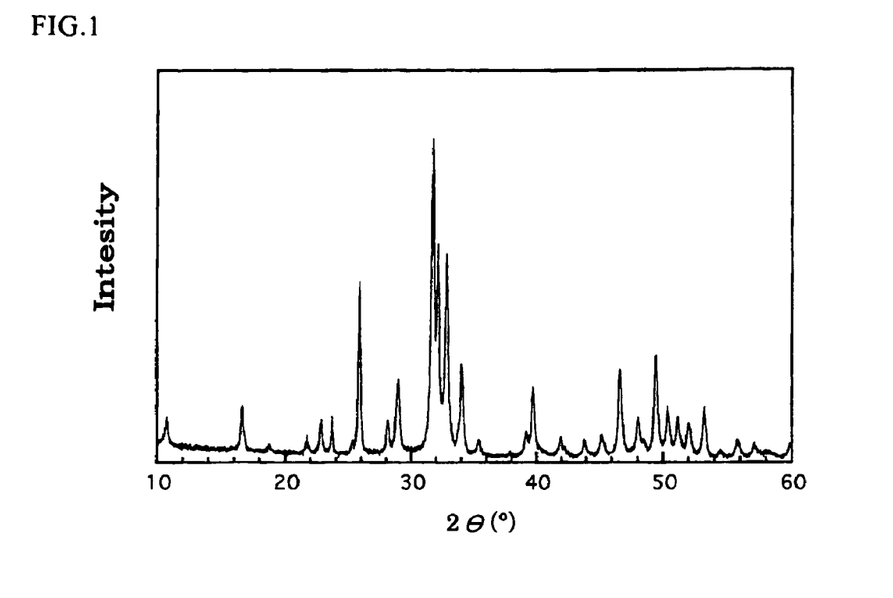
FIG. 1 illustrates a powder X-ray diffraction pattern of the bone substitute material for medical use produced in Example 1.
Figure 2:
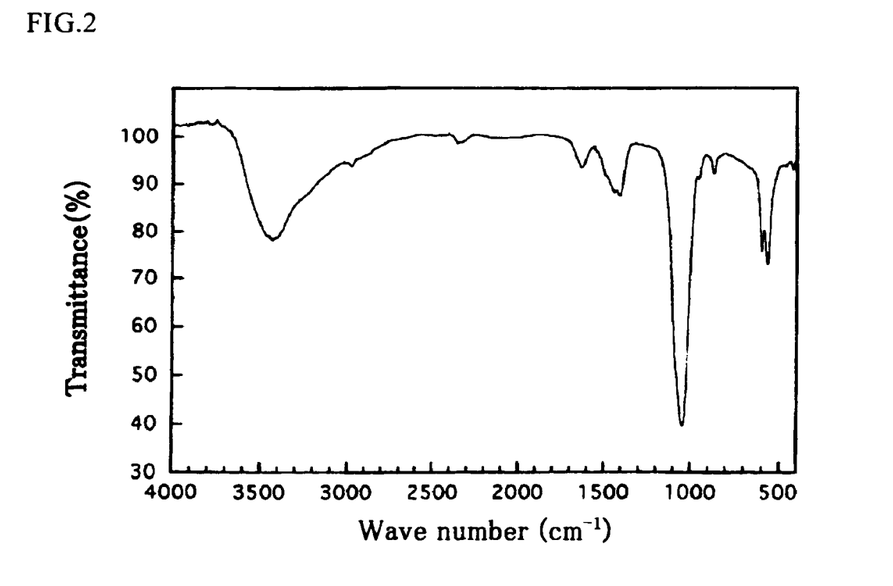
FIG. 2 illustrates a Fourier-transformed infrared spectrum of the bone substitute material for medical use produced in Example 1.

The X-ray diffraction pattern (FIG. 1) and the Fourier-transformed infrared spectrum (FIG. 2) of the block product showed that it was composed of carbonate apatite. It was also found by measurement with a CHN analyzer that the carbonate group content was 7% by weight. The indirect tensile strength of the bone substitute material produced was found to be 1.2 MPa. With respect to the powders having a particle size of 20 μm or smaller contained in the bone substitute material produced, the powder content was approx. 0.002% by weight.

The carbonate apatite blocks produced were inoculated with osteoblast cells, and cultivation was carried out. The osteocalcine value, a criterion for osteoconductivity, was 11 ng/ml on 15th day and markedly higher than the value of cell culture dish, 3 ng/ml, demonstrating that the product had osteoconductivity. The cultivation of osteoclast cells on the carbonate apatite blocks resulted in the formation of resorption cavities, suggesting that the bone substitute material had bone replacement capability. There was no indication of inflammation when the prosthesis material was implanted into a rat tibia. It was also recognized from the histopathological observation that there was induced osteoconduction with the carbonate apatite block produced.

Example 2

A mixture of an equal amount by weight of hemihydrated calcium sulfate (Nacalai Tesqui Inc.) and calcium carbonate (Nacalai Tesque Inc.) was kneaded with distilled water at a ratio of the water of 0.4 (ml/g) to produce calcium blocks. The thus produced calcium sulfate blocks were immersed in a 1M diammonium hydrogenphosphate solution (in which ammonium carbonate had been suspended) for two days at 80° C.

The X-ray diffraction pattern and the Fourier-transformed infrared spectrum of the block product showed that it was composed of carbonate apatite. It was also found by measurement with a CHN analyzer that the carbonate group content was 8% by weight. The indirect tensile strength of the bone substitute material produced was found to be 4.8 MPa. With respect to the powders having a particle size of 20 μm or smaller contained in the carbonate apatite block produced, the powder content was approx. 0.005% by weight.

The carbonate apatite blocks produced were inoculated with osteoblast cells, and cultivation was carried out. The osteocalcine value, a criterion for osteoconductivity, was 12 ng/ml on 15th day and markedly higher than the value of cell culture dish, 3 ng/ml, demonstrating that the product had osteoconductivity. The cultivation of osteoclast cells on the carbonate apatite blocks resulted in the formation of resorption cavities, suggesting that the bone substitute material produced has bone replacement capability. There was no indication of inflammation when the prosthesis material was implanted into a rat tibia. It was also recognized from the histopathological observation that there was induced osteoconduction with the carbonate apatite block produced.

Comparative Example 1

This example relates to the production of apatite block not containing carbonate group, in order to demonstrate the advantageous effects of the present invention.

Calcium sulfate (Nacalai Tesque Inc.) was kneaded with distilled water at a ratio of the water of 0.4 (ml/g) to produce calcium sulfate blocks. The thus produced calcium sulfate blocks were immersed in a 1M diammonium hydrogenphosphate solution (which had been nitrogen-replaced) for two days at 80° C.

The X-ray diffraction pattern and the Fourier-transformed infrared spectrum of the block product showed that it was composed of apatite not containing carbonate group. The indirect tensile strength of the bone substitute material produced was found to be 1.8 MPa. With respect to the powders having a particle size of 20 μm or smaller contained in the apatite block produced, the powder content was approx. 0.005% by weight.

The apatite blocks produced were inoculated with osteoblast cells, and cultivation was carried out. The osteocalcine value, a criterion for osteoconductivity, was 8 ng/ml on 15th day and markedly higher than that of cell culture dish, 3 ng/ml, showing that the product had osteoconductivity, but the value was lower than those with the bone substitute materials produced in Examples 1 and 2. No resorption cavities by osteoclast cells were observed, indicating that there was no bone replacement with the bone substitute material of this Comparative Example 1, which falls outside the scope of the present invention. There was no indication of inflammation when the prosthesis material was implanted into a rat tibia. It was also recognized from the histopathological observation that there was induced osteoconduction with the apatite block produced.

Example 3

Calcium hydroxide (Nacalai Tesque Inc.) 0.2 g was compression-molded in a circular mold at an axial compression pressure of 20 kg/cm$^2$ and the resultant compressed body was subjected to carbonation under a stream of carbon dioxide with a relative humidity of 100% to produce calcium carbonate blocks. The X-ray diffraction pattern and the Fourier-transformed infrared spectrum of the block product showed that it was composed of calcium carbonate. The calcium carbonate blocks were immersed in a 1M disodium hydrogenphosphate solution at 60° C. for seven days, to produce blocks in the same shape with the calcium carbonate block.

Figure 3:
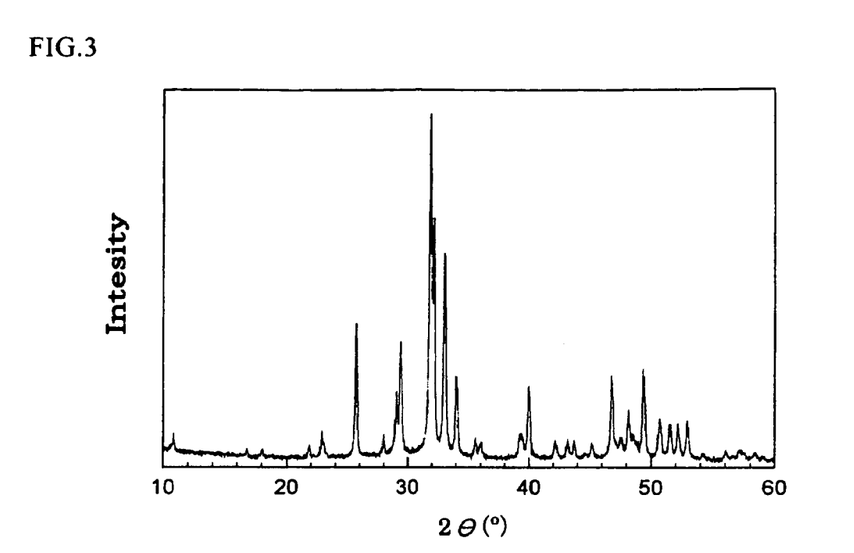
FIG. 3 illustrates a powder X-ray diffraction pattern of the bone substitute material for medical use produced in Example 3.
Figure 4:
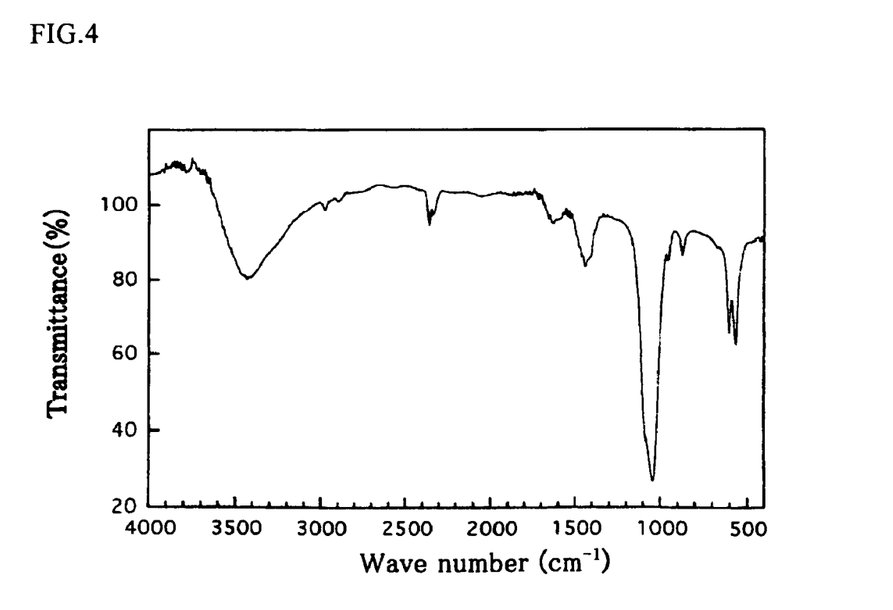
FIG. 4 illustrates a Fourier-transformed infrared spectrum of the bone substitute material for medical use produced in Example 3.

The X-ray diffraction pattern (FIG. 3) and the Fourier-transformed infrared spectrum (FIG. 4) of the block product showed that it was composed of carbonate apatite. It was also found by measurement with a CHN analyzer that the carbonate group content was 11% by weight. The indirect tensile strength of the bone substitute material produced was found to be 1.8 MPa. With respect to the powders having a particle size of 20 μm or smaller contained in the carbonate apatite block produced, the powder content was approx. 0.005% by weight.

The carbonate apatite blocks produced were inoculated with osteoblast cells, and cultivation was carried out. The osteocalcine value, a criterion for osteoconductivity, was 13 ng/ml on 15th day and markedly higher than the value of cell culture dish, 3 ng/ml, demonstrating that the product had osteoconductivity. The cultivation of osteoclast cells resulted in the formation of resorption cavities, suggesting that the bone substitute material produced had bone replacement capability. There was no indication of inflammation when the prosthesis material was implanted into a rat tibia. It was also recognized from the histopathological observation that there was induced osteoconduction with the carbonate apatite block produced.

Comparative Example 2

This example relates to the production of sintered hydroxyapatite which does not contain carbonate group, in order to demonstrate the advantageous effects of the present invention.

Hydroxyapatite powders (Taihei Chemicals Ltd.) were compression-molded at an axial pressure of 20 kg/cm². The resultant compressed body was heated up to 0.1250° C. at the rate of 4° C. per minute and maintained at 1250° C. for six hours, followed by cooling to produce sintered hydroxyapatite.

Figure 5:
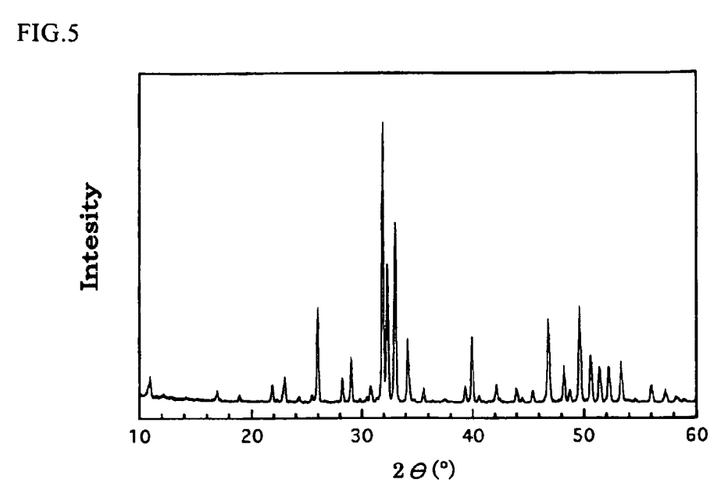
FIG. 5 illustrates a powder X-ray diffraction pattern of the bone substitute material for medical use produced in Comparative Example 2.
Figure 6:
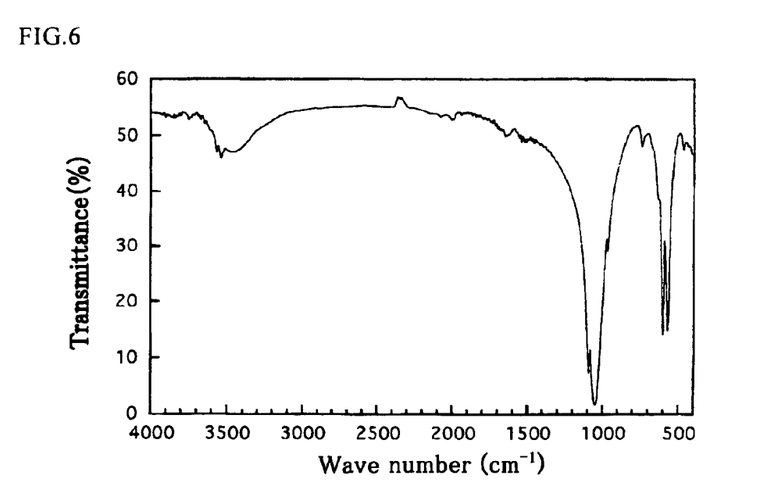
FIG. 6 illustrates a Fourier-transformed infrared spectrum of the bone substitute material for medical use produced in Comparative Example 2.

The X-ray diffraction pattern (FIG. 5) and the Fourier-transformed infrared spectrum (FIG. 6) of the sintered hydroxyapatite body produced showed that it was composed of apatite not containing carbonate group. The indirect tensile strength of the bone substitute material produced was found to be 90 MPa. With respect to the powders having a particle size of 20 μm or smaller contained in the apatite block produced, the powder content was approx. 0.001% by weight.

The apatite blocks produced were inoculated with osteoblast cells, and cultivation was carried out. The osteocalcine value, a criterion for osteoconductivity, was carried out. The osteocalcine value, a criterion for osteoconductivity, was 8 ng/ml on 15th day and markedly higher than that of cell culture dish, 3 ng/ml, showing that the product had osteoconductivity but the value was lower than those with the bone substitute materials produced in Example 1, 2 and 3. No resorption cavities by osteoclast cells were observed, indicating that there was no bone replacement with the bone substitute material produced in this Comparative Example 2, which falls outside the scope of the present invention. There was no indication of inflammation when the prosthesis material was implanted into a rat tibia. It was also recognized from the histopathological observation that there was induced osteoconduction with the apatite block produced.

Comparative Example 3

This example relates to the production of apatite block from a naturally occurring material, in order to demonstrate the advantageous effects of the present invention: Ground natural limestones having a particle size of about 1 mm were immersed in a 1M disodium hydrogenphosphate solution at 60° C. for seven days to produce blocks in the same shape with the starting ground limestones.

The X-ray diffraction pattern and the Fourier-transformed infrared spectrum of the block product showed that it was composed of carbonate apatite. It was also found by measurement with a CHN analyzer that the carbonate group content was 10% by weight. With respect to the powders having a particle size of 20 μm or smaller contained in the carbonate apatite block produced, the powder content was approx. 1.2% by weight. On implanting the product into a rat tibia, there was observed clear indication of inflammation presumably due to impurities inherently contained in the naturally occurring material. From the histological observation there was recognized no osteoconduction with the carbonate apatite block product.

Comparative Example 3-2

This example relates to the production of carbonate apatite block falling outside the scope of the present invention, in order to demonstrate the advantageous effects of the present invention, particularly in terms of the state of the powder. For the purpose of removing powders having a particle size of 20 μm or smaller contained in the carbonate apatite blocks as produced in Comparative Example 3, the carbonate apatite blocks produced were placed on a 140-mesh sieve, followed by flushing with water so that fine powders passed through the sieve. The carbonate apatite blocks remaining on the sieve were dried. The thus produced carbonate apatite block had a powder content of approximately 0.05% by weight with respect to the powders having a particle size of 20 μm or smaller.

On implanting the product into a rat tibia, there was observed a clear indication of inflammation presumably due to impurities inherently contained in the naturally occurring material. While the inflammation was mild as compared with that in Comparative Example 3, from the histological observation there was recognized no osteoconduction with the carbonate apatite product here again.

Example 4

α-tricalcium phosphate powders (Taihei Chemicals Ltd.) were admixed with water at a ratio of 1:1 by weight to prepare a suspension. Polyurethane foam (Bridgestone Corp.) was immersed in the suspension of α-tricalcium phosphate powders, followed by drying. The thus prepared polyurethane foam with the α-tricalcium phosphate powders adhered to the trabeculae thereof was calcined at 1500° C. for five hours by raising the temperature at the rate of 1° C. per minute up to 400° C. and then at the rate of 5° C., whereafter the calcined product was cooed. Thus, there was produced sintered α-tricalcium phosphate foam.

The α-tricalcium phosphate foam produced was immersed in an aqueous solution in which are suspended sodium carbonate and disodium hydrogen phosphate, to undergo hydrothermal treatment at 200° C. for twelve hours.

Figure 7:
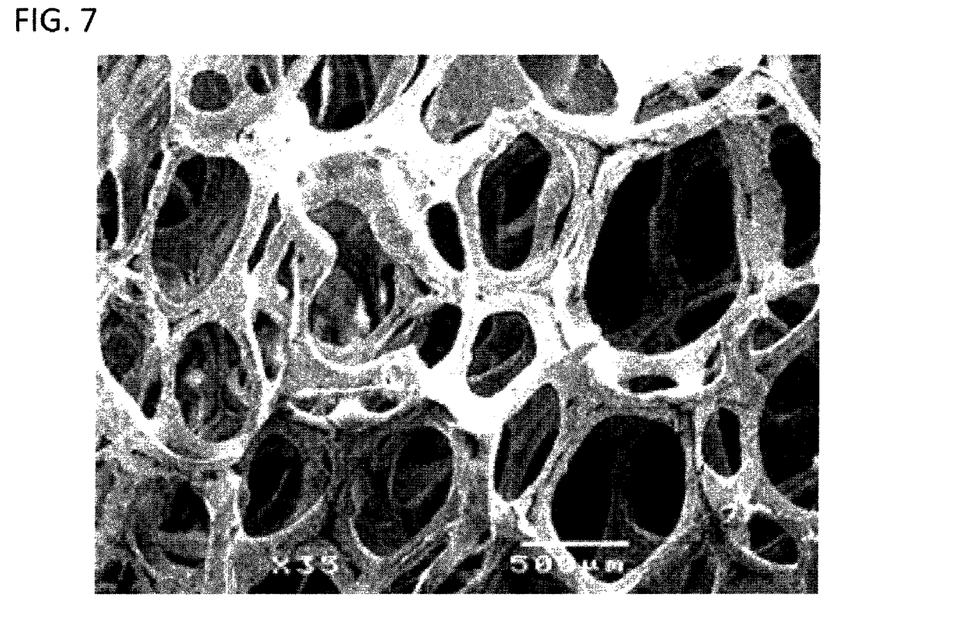
FIG. 7 shows an electron microscope photograph of the bone substitute material produced in Example 4.
Figure 8:
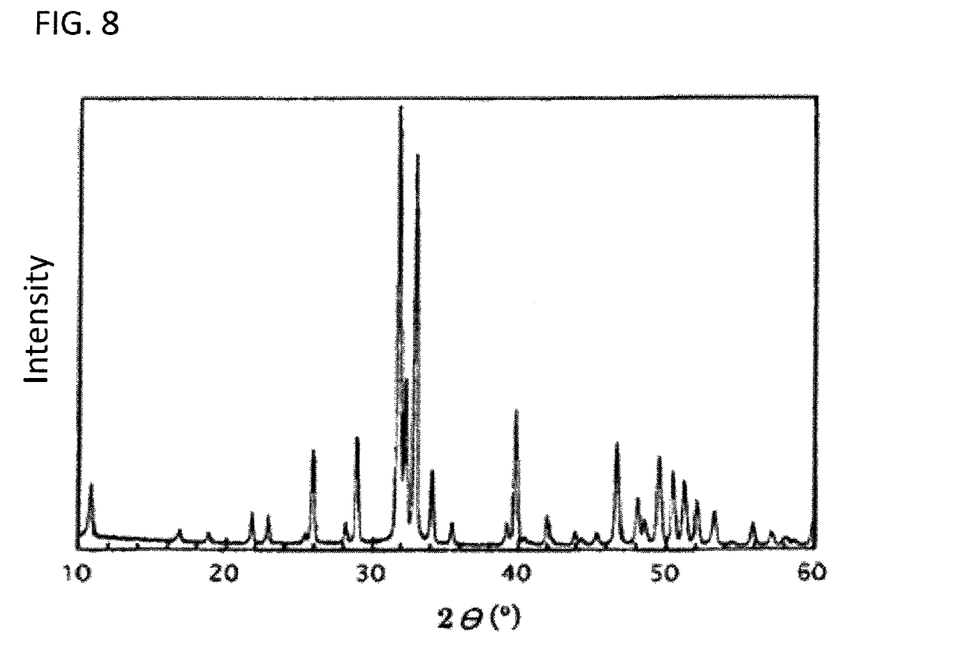
FIG. 8 illustrates a powder X-ray diffraction pattern of the bone substitute material for medical use produced in Example 4.
Figure 9:
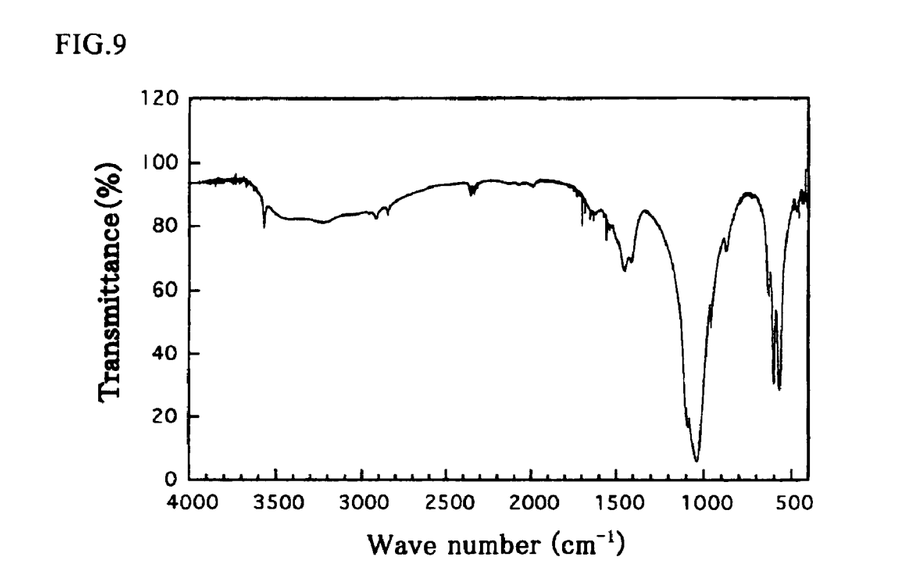
FIG. 9 illustrates a Fourier-transformed infrared spectrum of the bone substitute material for medical use produced in Example 4.

FIG. 7 shows the foamed compound obtained. The X-ray diffraction pattern (FIG. 8) and the Fourier-transformed infrared spectrum (FIG. 9) of the foamed compound showed that it was composed of carbonate apatite. It was also found by measurement with a CHN analyzer that the carbonate group content was 6% by weight. The indirect tensile strength was found to be 0.3 MPa. With respect to the powders having a particle size of 20 μm or smaller contained in carbonate apatite block produced, the power content was approx. 0.001% by weight.

The carbonate apatite blocks produced were inoculated with osteoblast cells, and cultivation was carried out. The osteocalcine value, a criterion for osteoconductivity, was 13 ng/ml on 15th day and markedly higher than the value of cell culture dish, 3 ng/ml, demonstrating that the product had osteoconductivity. The formation of resorption cavities by osteoclast cells indicated that the bone substitute material produced had bone replacement capability. There was no indication of inflammation when the prosthesis material was implanted into a rat tibia. It was also recognized from the histopathological observation that there was induced osteoconduction with the carbonate apatite block produced.

Comparative Example 4

This example relates to the production of carbonate apatite foam by sintering process, which process falls outside the scope of the present invention, in order to demonstrate the advantageous effects of the present invention. The starting carbonate apatite powders were synthesized by wet process: Five liters of a sodium hydrogencarbonate solution, prepared by dissolving sodium hydrogencarbonate in an aqueous solution of 0.6 moles of sodium hydrogenphosphate, and five liters of a 1M calcium acetate aqueous solution were concurrently added dropwise to three liters of ion-exchanged water kept at 80° C., while controlling the pH of the ion-exchanged water to be 9.0 to 9.5. On completing the dropwise addition, the resultant was maintained at 80° C. for twelve hours for aging, followed by filtration and washing operations so as to remove $Na^+$ ions. The thus obtained powders were dried at 110° C. for twenty-four hours. The X-ray diffraction pattern and the Fourier-transformed infrared spectrum of the powder product showed that it was composed of carbonate apatite. It was also shown found by measurement with a CHN analyzer that the carbonate group content was 9% by weight.

The carbonate apatite powders produced were admixed with distilled water at a ratio of 1:1 to prepare a suspension. Polyurethane foam (Bridgestone Corp.) was immersed in the suspension of carbonate apatite powders, followed by drying. The thus prepared polyurethane foam with the carbonate apatite powders adhered to the trabeculae thereof was calcined at 900° C. for five hours by raising the temperature at the rate of 1° C. per minute up to 400° C. and then at the rate of 5° C., whereafter the calcined product was cooled. Although it was confirmed that there was formed a foamed structure in the furnace, it collapsed upon removal from the furnace. It was thus evidenced that it is not possible to produce a desired carbonate apatite foam. The results are similar even with a calcination temperature of 1000° C., 1100° C., 1200° C. or 1300° C.

Comparative Example 5

This example relates to the production of carbonate apatite foam by sintering process, which process falls outside the scope of the present invention, in order to demonstrate the advantageous effects of the present invention.

The carbonate apatite powders prepared in Comparative Example 3 were admixed with distilled water at a ratio of 1:1 to prepare a suspension. Polyurethane foam (Bridgestone Corp.) was immersed in the suspension of carbonate apatite powders, followed by drying. The thus prepared polyurethane foam with the carbonate apatite powders adhered to the trabeculae thereof was calcined at 1400° C. for five hours by raising the temperature at the rate of 1° C. per minute up to 400° C. and then at the rate of 5° C. per minute, whereafter the calcined product was cooled. Although the product was fragile, removal from the furnace was managed. The X-ray diffraction pattern and the Fourier-transformed infrared spectrum of the product showed that it was composed of hydroxyapatite, and it was also found that the product contained no carbonate group by a CHN analyzer. No resorption cavities by osteoclast cells were observed, indicating that there was no induced bone replacement with the bone substitute material produced.

Comparative Example 6

In order to demonstrate the advantageous effects of the present invention, the carbonate apatite powder produced in Comparative Example 4 (having an average particle size of 1 μm or smaller) was implanted into bone defect site formed in a rat tibia. In two days from the implantation there was a clear indication of inflammation, i.e., the skin at the implantation site became swollen. On incising the skin, there was observed a humoral yellowish transparent effusion. There were no carbonate apatite powder present in the bone defect site, and no indication of osteoconduction whatsoever.

What is claimed is:

1. A method of producing a bone substitute material in the form of a block predominantly composed of carbonate apatite for medical use, which comprises the step of forming carbonate apatite by contacting a porous block of calcium compound with a phosphate-containing solution, wherein said porous calcium compound block contains substantially no powders such that powders with a diameter of 20 micrometers or smaller are less than 1.0% by weight of said porous calcium compound block, wherein at least one of said porous calcium compound block and said phosphate solution contains a carbonate group, and wherein the method does not include any sintering step, and wherein the porous block of calcium compound is one prepared using an artificially synthesized calcium compound, the porous block having an average pore diameter in a range of 50-1000 μm.

2. The method of producing a bone substitute material for medical use as claimed by claim 1, wherein the calcium compound block prepared using an artificially synthesized calcium compound is a foamed calcium compound.

3. The method of producing a bone substitute material for medical use as claimed in claim 1, wherein the contacting of the block of calcium compound with the phosphate-containing solution comprises immersing the block in the phosphate-containing solution.

4. The method of producing a bone substitute material for medical use as claimed by claim 1, wherein said calcium compound block contains substantially no powders such that powders with a diameter of 20 micrometers or smaller are less than 0.8% by weight.

5. The method of producing a bone substitute material of claim 1, wherein said calcium compound block contains calcium sulfate.

6. The method of producing a bone substitute material of claim 5, wherein said phosphate solution contains a carbonate group.

7. The method of producing a bone substitute material of claim 6, wherein said phosphate solution contains ammonium carbonate.

8. The method of producing a bone substitute material of claim 5, wherein said calcium compound block also contains calcium carbonate.

9. The method of producing a bone substitute material of claim 1, wherein said calcium compound block is a tricalcium phosphate block and wherein said phosphate solution contains a carbonate group.

10. The method of producing a bone substitute material of claim 9, wherein said phosphate solution contains ammonium carbonate.

11. A bone substitute material produced by a method comprising forming carbonate apatite by contacting a porous block of calcium compound with a phosphate-containing solution, wherein said porous calcium compound block contains substantially no powders such that powders with a diameter of 20 micrometers or smaller are less than 1.0% by weight, wherein at least one of said porous calcium compound block and said phosphate solution contains a carbonate group, and wherein the method does not include any sintering step, and wherein the bone substitute material is predominantly composed of carbonate apatite, and wherein the porous block of calcium compound is one prepared using an artificially synthesized calcium compound, the porous block having an average pore diameter in a range of 50-1000 µm.

12. A bone substitute material claimed in claim 11, wherein the calcium compound block prepared using an artificially synthesized calcium compound is a foamed calcium compound.

13. A method of producing a bone substitute material predominantly composed of carbonate apatite, comprising:
    providing a porous body formed of a calcium compound, the body containing substantially no powders and having an average pore diameter in a range of 50-1000 µm;
    contacting the porous body with a phosphate-containing solution, at least one of said porous body and said phosphate solution containing a carbonate group, whereby the porous body is predominantly composed of carbonate apatite; and
    wherein the method does not include any sintering step.

14. The method of producing a bone substitute material of claim 13, wherein the block of calcium compound is one prepared using an artificially synthesized calcium compound.

* * * * *